(12) United States Patent
Haglund, Jr. et al.

(10) Patent No.: US 6,825,045 B2
(45) Date of Patent: Nov. 30, 2004

(54) SYSTEM AND METHOD OF INFRARED MATRIX-ASSISTED LASER DESORPTION/ IONIZATION MASS SPECTROMETRY IN POLYACRYLAMIDE GELS

(75) Inventors: Richard F. Haglund, Jr., Brentwood, TN (US); David R. Ermer, Mississippi State, MS (US); Michelle Lee Baltz-Knorr, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 346 days.

(21) Appl. No.: 09/931,490

(22) Filed: Aug. 16, 2001

(65) Prior Publication Data

US 2002/0076824 A1 Jun. 20, 2002

Related U.S. Application Data

(60) Provisional application No. 60/225,719, filed on Aug. 16, 2000.

(51) Int. Cl.$^7$ .......................... G01N 1/00; G01N 33/48; B01D 59/44
(52) U.S. Cl. ....................... 436/174; 250/281; 250/282; 250/288; 436/86; 436/87; 436/88; 436/89; 436/90; 436/91; 436/92; 436/93; 436/94; 436/173; 436/175; 436/176; 436/181
(58) Field of Search .................... 436/86–94, 173–176, 436/181; 250/281–282, 288

(56) References Cited

U.S. PATENT DOCUMENTS

| | | | |
|---|---|---|---|
| 5,118,937 A | | 6/1992 | Hillenkamp et al. |
| 5,498,545 A | * | 3/1996 | Vestal .......................... 436/47 |
| 5,643,800 A | | 7/1997 | Tarantino et al. |

(List continued on next page.)

FOREIGN PATENT DOCUMENTS

| | | | |
|---|---|---|---|
| EP | 964427 | * | 12/1999 |
| GB | 2340298 | * | 2/2000 |
| WO | WO 99/57318 | | 11/1999 |

OTHER PUBLICATIONS

Loo, R. R. O. et al, Techniques in Protein Chemistry VII, [Symposium of the Protein Society], 9th, Boston, Jul. 8–12, 1996, Meeting Date 1995, 305–313, Editor: Marshak, D, R., Publisher: Academic, San Diego, Calif.*

Loo, Rachel R. O. et al, Mass Spectrometry of Biological Materials (2nd Edition) 1998, 325–343, Editors: Larsen, B. S. et al, Publisher: Dekker, New York, N. Y.*

(List continued on next page.)

*Primary Examiner*—Arlen Soderquist
(74) *Attorney, Agent, or Firm*—Morris, Manning & Martin; Tim Tingkang Xia, Esq.

(57) ABSTRACT

A system and method for desorption and ionization of analytes in an ablation medium. In one embodiment, the method includes the steps of preparing a sample having analytes in a medium including at least one component, freezing the sample at a sufficiently low temperature so that at least part of the sample has a phase transition, and irradiating the frozen sample with short-pulse radiation to cause medium ablation and desorption and ionization of the analytes. The method further includes the steps of selecting a resonant vibrational mode of at least one component of the medium and selecting an energy source tuned to emit radiation substantially at the wavelength of the selected resonant vibrational mode. The medium is an electrophoresis medium having polyacrylamide. In one embodiment, the energy source is a laser, where the laser can be a free electron laser tunable to generate short-pulse radiation. Alternatively, the laser can be a solid state laser tunable to generate short-pulse radiation. The laser can emit light at various ranges of wavelength.

32 Claims, 10 Drawing Sheets

U.S. PATENT DOCUMENTS

| | | | |
|---|---|---|---|
| 5,828,063 | A | 10/1998 | Köster et al. |
| 6,020,208 | A | 2/2000 | Hutchens et al. |
| 6,057,543 | A | 5/2000 | Vestal et al. |
| 6,071,610 | A | 6/2000 | Jarrell et al. |
| 6,104,028 | A | 8/2000 | Hunter et al. |
| 6,140,053 | A | 10/2000 | Köster |
| 6,140,639 | A | 10/2000 | Gusev et al. |
| 6,143,085 | A | 11/2000 | Marsh |

OTHER PUBLICATIONS

Menzel, C. et al, Rapid Communicaitons in Mass Spectrometry 1999, 13, 26–32.*

Mortz, E. et al, Biological Mass Spectrometry 1994, 23, 249–261.*

Krutchinsky, A. N. et al, Journal of Mass Spectrometry 1995, 30, 375–379.*

Loo, R. R. O. et al, Electrophoresis 1997, 18), 382–390.*

Strahler, J. R. et al, International Journal of Mass Spectrometry and Ion Processes 1997, 169/170, 111–126.*

Eckerskorm, C. et al, ;Analytical Chemistry 1997, 69, 2888–2892.*

Cramer et al. Matrix–Assisted Laser Desorption and Ionization in the O–H and C=O Absorption Bands of Alphatic and Aromatic Matrixes: Dependence on Laser Wavelength and Temporal Beam Profile, *Intl. J. Mass Spectrom.*, Ion Processes, 169–170:51–67 (1997).

Hess et al. "IR–MALDI of Low Molecular Weight Compounds Using a Free Electron Laser," *App. Surf. Sci.*, 127–129:235–241 (1998).

Becker et al. "Broadband Pockels Cell and Driver for a Mark III–Type Free–Electron Laser," *Rev. Sci. Intrum.*, 65:1496–1501 (1994).

Blackstock et al. "Proteomics: Quantitative and Physical Mapping of Cellular Proteins," *Trends in Biotech*, 17:121–127 (1999).

Brau. "Free–Electron Lasers," *Science*, 239:1115–1121 (1988).

Cohen et al. "Mass Spectrometry of Whole Proteins Eluted from Sodium Dodecyl Sulfate–Polyacrylamid Electrophoresis Gels," *Anal. Biochem.*, 24(7):257–267 (1997).

Edwards et al. "Free–Electron Lasers: Reliability, Performance and Beam Delivery," *IEEE J. Sel. Topics in Quantum Electron.*, 2(4):810–817 (1996).

Ermer et al. "Charged Particle Emission from Dielectric Materials initiated By a Turnable Picoseceon Mid–Infrared Laser," *Proc. of SPIE—Intl. Soc. For Opt. Eng.*, 3935:104–112 (2000).

Henzel et al. "Identifying Proteins from Two–Dimensional Gels by Molecular Mass Seaching of Peptide Fragments in Protein Sequence Databases," *Proc. Natl. Acad. Sci. USA*, 90:5011–5015 (1993).

Haglund et al. "Explosive Vaporization in Fused Silica Initiated by a Tunable Infrared Laser," *App. Sur. Sci.*, 168:258–262 (2000).

Haglund. "Mechanisms of Laser–Induced Desorption and Ablation," *Laser Ablation and Desorption*, Academic Press, Boston, Exp. Meth. Phys. Sci. 30:15–138 (1998).

Liang et al. "Characterization of SDS–PAGE–Separated Proteins by Matrix–Assisted Laser Desorption/Ionization Mass Spectrometry," *Anal. Chem.*, 68:1012–1018 (1996).

Loo et al. "High Sensitivity Mass Spectrometric Methods for Obtaining Intact Molecular Weights ftrom Gel–Separated Proteins," *Electrophoresis*, 20:743–748 (1999).

Loo et al. "Mass Spectrometry of Proteins Directly From Polyacrylamide Gels," *Anal. Chem.*, 68(11):1910–1917 (1996).

Strupat et al. "Matrix–Assisted Laser Desorption Ionization Mass–Spectrometry of Proteins Electroblotted After Polyacrylamid–Gel Electrophoresis," *Anal. Chem.*, 66:464–470 (1994).

Vertes et al. "Laser–Induced Thermal Desorption and Matrix–Assisted Methods," *Laser Isonization Mass Analysis*, Wiley Interscience, New York, Chem. Anal. Series, 124:127–175 (1993).

* cited by examiner

SYSTEM AND METHOD OF INFRARED MATRIX-ASSISTED LASER DESORPTION/IONIZATION MASS SPECTROMETRY IN POLYACRYLAMIDE GELS

CROSS-REFERENCE TO RELATED APPLICATION

This application claims priority to U.S. Provisional Application Ser. No. 60/225,719, which was filed on Aug. 16, 2000, in the United States Patent and Trademark Office.

This invention was made with Government support under a contract awarded by the U.S. Department of Navy and a contract awarded by the U.S. Department of Energy, respectively, and the Government has certain rights in this invention.

BACKGROUND OF THE INVENTION

1. Field of the Invention

The present invention generally relates to a system and method for desorption and ionization of analytes in a medium. More particularly, the present invention relates to a system and method for infrared matrix-assisted laser desorption and ionization mass spectrometry of analytes in a medium such as polyacrylamide gels.

2. Description of the Related Art

The recent sequencing of the human genome is accelerating the need to understand the variety, characteristics, and functions of the numerous proteins expressed by the genomes of humans and other organisms in response to internal and external stimuli. The characterization of proteins, such as their structure and function, is commonly referred to as proteomics. Mass spectrometry ("MS") has proven to be an invaluable tool for proteomics, making possible the accurate profiling of proteins, polypeptides, peptides and other factors by precision measurements of molecular ion masses. Polyacrylamide gel electrophoresis ("PAGE") and related electrophoretic techniques are invaluable tools for the analysis of proteins, nucleic acids and other factors. Using PAGE techniques coupled with experimental manipulation and/or labeling techniques, it is possible to characterize structurally and functionally a variety of cellular determinants.

The ability to combine the preliminary separation provided by PAGE and resolution of MS into a coupled PAGE-MS system is highly desirable. Specifically, matrix-assisted laser desorption and ionization (MALDI) mass spectrometry is generally acknowledged to be an integral part of any integrated strategy for proteomics, as discussed in the article "Proteomics: quantitative and physical mapping of cellular proteins," Blackstock et al., Trends in Biotech 17: 121–127 (1999). However, previous attempts to examine proteins by PAGE-MS or MALDI-MS required one or more of following limitations: (1) extraction of the protein from the polyacrylamide gel followed by routine sample preparation for MS; (2) transfer of the protein from the gel onto a membrane and permeation of the sample and membrane with a matrix for MALDI-MS; and/or (3) dehydration of the polyacrylamide gel and permeation or coating of the gel with a MALDI matrix.

The article "Mass spectrometry of whole proteins eluted from sodium dodecyl sulfate-polyacrylamide electrophoresis gels," Cohen et al., Anal. Biochem. 247(2): 257–267 (1997), describes the use of mass spectrometry in the analysis of proteins eluted from SDS-PAGE gels using a 4-HCCA matrix and a fixed-wavelength laser operating in the ultraviolet range.

Researchers have described a method for identifying proteins from two-dimensional gels by electroblotting the proteins from the gels onto a membrane in the article "Identifying proteins from two-dimensional gels by molecular mass searching of peptide fragments in protein sequence databases," Henzel et al., Proc. Natl. Acad. Sci. USA 90: 5011–5015 (1993). The proteins were located by staining with Coomassie brilliant blue. Protein spots of interest were eluted from the membrane, trypsin digested, and analyzed by capillary high-performance liquid chromatography (HPLC), peptide mapping, and automated protein sequencing using the Edmond method. Mass spectrometry was performed by reconstituting an aliquot of the tryptic digest with a MALDI matrix and applying the sample to a mass spectrometer probe tip. The laser for the mass spectrometer was operated in the ultraviolet range at 337 nanometers (nm). The proteins and peptide fragments were identified by searching for the mass spectra of the ionization products in peptide fragment and protein sequence databases.

A technique described in "Matrix-assisted laser desorption ionization mass-spectrometry of proteins electroblotted after polyacrylamide-gel electrophoresis," Strupat et al., Anal. Chem. 66: 464–470 (1994), was used to obtain MS signals of proteins physically transferred from a polyacrylamide gel to a membrane, wherein the samples were then treated with succinic acid, using a 100-nanosecond (ns) pulse from an Er:YAG laser operated at a fixed wavelength of 2.94 micrometer ($\mu$m). These researchers attempted to do MALDI-MS, using an Er: YAG laser, directly from the polyacrylamide gel, both with and without the addition of exogenous matrix, but were unsuccessful.

Additional publications describe minor variations of these same techniques. The article "Characterization of SDS-PAGE-separated proteins by matrix-assisted laser desorption/ionization mass spectrometry," Liang et al., Anal. Chem. 68: 1012–1018 (1996), describes MALDI-MS performed on proteins on nitrocellulose membranes using a frequency-tripled Nd:YAG laser operating at a fixed wavelength of 355 nm.

The paper "Mass spectrometry of proteins directly from polyacrylamide gels," Ogorzalek Loo et al., Anal. Chem. 68:1910–1917 (1996), described preparing a protein sample on a polyacrylamide gel, identifying bands by staining or comparison to an identical stained gel, dehydrating the gel, adding a MALDI matrix (sinapinic acid) to gel positions of interest, irradiating the MALDI matrix with 337 nm laser light, and analyzing the products in a time-of-flight (TOF) mass spectrometer. The same group of researchers later described a variant of MALDI-MS performed on slices of polyacrylamide gel soaked in sinapinic acid in the article "High sensitivity mass spectrometric methods for obtaining intact molecular weights from gel-separated proteins," Loo et al., Electrophoresis 20: 743–748 (1999).

Among other disadvantages, all of these techniques at least require considerable sample handling procedures that are impractical for adaptation to future designs for high-throughput sample analysis procedures. Therefore, there exists a need for an improved system and method for desorption and ionization of analytes in a medium. In particular, there is a need for an improved system and method that can allow direct high-speed sampling and analysis of proteins from polyacrylamide and other electrophoretic gels.

SUMMARY OF THE INVENTION

The present invention is related to a system and method for desorption and ionization of analytes in an ablation medium. In one aspect of the present invention, there is provided a method for desorption and ionization of analytes including the steps of preparing a sample comprising analytes in a medium having at least one component, selecting a resonant vibrational mode of at least one component of the medium, selecting a laser tuned to emit light substantially at the wavelength of the selected vibrational mode, and irradiating the sample with the laser light to cause medium ablation and desorption and ionization of the analytes. The method further includes the steps of passing the ionized analytes through a mass spectrometer, and obtaining a mass spectrum of the ionized analytes. The medium can be an electrophoresis medium that is in the form of an electrophoresis gel. The medium may also be chosen from, but is not limited to, materials such as cellulose acetate, paper, agarose an the like.

In another aspect, the present invention relates to a method for desorption and ionization of analytes including the steps of preparing a sample having analytes and a polyacrylamide medium having at least one component, selecting a resonant vibrational mode of at least one component of the medium, selecting a laser tuned to emit light substantially at the wavelength of the selected vibrational mode, and irradiating the sample with laser light to cause medium ablation and desorption and ionization of the analytes. In one embodiment, the sample is irradiated by laser light delivered in pulses, each pulse having duration of less than 5.0 picoseconds (ps), where the pulses are separated in time by more than 100 ps. The method further includes the steps of passing the ionized analytes through a mass spectrometer, and obtaining a mass spectrum of the ionized analytes.

In a further aspect, the present invention relates to a method for desorption and ionization of analytes including the steps of preparing a sample having analytes in a medium including at least one component, freezing the sample at a sufficiently low temperature so that at least part of the sample has an increase in viscosity and a decrease in vapor pressure, and irradiating the frozen sample with short-pulse radiation to cause medium ablation and desorption and ionization of the analytes. The method further includes the steps of selecting a resonant vibrational mode of at least one component of the medium and selecting an energy source tuned to emit short-pulse radiation substantially at the wavelength of the selected resonant vibrational mode.

In one embodiment, the energy source is a laser, where the laser can be a free electron laser tunable to generate short-pulse radiation. Alternatively, the laser can be a solid state laser tunable to generate short-pulse radiation. Moreover, the laser can be a gas laser or a metal vapor laser. The laser can emit light at various ranges of wavelength including a range of wavelength greater than 4.5 $\mu$m and less than 10.0 $\mu$m, a range of wavelength greater than 5.7 $\mu$m and less than 6.5 $\mu$m, a range of wavelength greater than 6.7 $\mu$m and less than 7.3 $\mu$m, and/or a range of wavelength greater than 7.3 $\mu$m and less than 9.8 $\mu$m.

In another embodiment, a resonant vibrational mode of at least one component of the medium can be selected from an absorption spectrum of the medium such as a Fourier-transform infrared absorption spectrum of the medium. The medium can be an electrophoresis medium that includes polyacrylamide. The medium can be in the form of a gel. The medium can also be chosen from materials such as cellulose acetate, paper, agarose and the like.

In yet another embodiment, by placing the sample in a sample support and immersing the sample support in liquid nitrogen for a period of time the sample may be cooled or frozen at a sufficiently low temperature such that any water within the sample may undergo a phase transition to change to ice.

In another embodiment, the sample may be prepared by spatially separating the analytes within a medium by electrophoresis. Moreover, the sample may be irradiated by sequentially irradiating a plurality of positions within the sample, wherein at least two irradiated positions correspond to the locations of the spatially separated analytes. Each of the plurality of positions is irradiated by radiation delivered in pulses, each pulse having a duration of less than the relaxation time of a selected vibrational mode of at least one component of the medium. The pulses are separated in time by intervals, each interval having a duration of at least ten times the relaxation time of the selected vibrational mode. Alternatively, each pulse may have a duration of less than the thermal or mechanical relaxation time of the at least one component of the medium. In one embodiment, moreover, the sample is moved in a motion back and forth relative to the laser light to form a rastering trace such that the desorption and ionization of the analytes occur substantially at a same region in space such as a region around the focal point of the laser light.

In yet another aspect, the present invention relates to a system for desorption and ionization of analytes. The system includes means for preparing a sample comprising analytes in a medium having at least one component, means for selecting a resonant vibrational mode of at least one component of the medium, means for emitting light substantially at the wavelength of the selected vibrational mode, and means for irradiating the sample to cause medium ablation and desorption and ionization of the analytes. The system further includes means for freezing the sample to a sufficiently low temperature so that at least part of the sample has an increase in viscosity and a decrease in vapor pressure, and means for delivering light in pulses, each pulse having a duration of less than the relaxation time of the selected vibrational mode, wherein the pulses are separated in time by intervals, each interval having a duration of at least ten times the relaxation time of the selected vibrational mode. Alternatively, each pulse may have a duration of less than the thermal or mechanical relaxation time of the at least one component of the medium. In one embodiment, moreover, the sample is moved back and forth relative to the laser light to form a rastering trace such that the desorption and ionization of the analytes occur substantially at a same region in space such as a region around the focal point of the laser light.

In a further aspect, the present invention relates to a system for desorption and ionization of analytes. The system includes means for preparing a sample having analytes and a polyacrylamide medium having at least one component, means for selecting a resonant vibrational mode of at least one component of the medium, means for emitting light substantially at the wavelength of the selected vibrational mode, and means for irradiating the sample with laser light to cause medium ablation and desorption and ionization of the analytes. Moreover, the system includes means for stabilizing the sample for compatibility with high-vacuum conditions and means for delivering light in pulses, each pulse having a duration of less than the relaxation time of the selected vibrational mode, wherein the pulses are separated in time by intervals, each interval having a duration of at least ten times the relaxation time of the selected vibrational mode. Alternatively, each pulse may have a duration of less than the thermal or mechanical relaxation time of the at least one component of the medium. In one embodiment, moreover, the sample is moved in a motion back and forth relative to the laser light to form a rastering trace such that the desorption and ionization of the analytes occur substantially at a same region in space such as a region around the focal point of the laser light.

In yet a further aspect, the present invention relates to a system for desorption and ionization of analytes. The system includes means for preparing a sample having analytes in a medium including at least one component, means for freezing the sample to a sufficiently low temperature so that at least part of the sample has an increase in viscosity and a decrease in vapor pressure, and means for irradiating the chilled sample with short-pulse radiation to cause medium ablation and desorption and ionization of the analytes. Additionally, the system includes means for selecting a resonant vibrational mode of at least one component of the medium, and means for tuning an energy source to emit short-pulse radiation substantially at the wavelength of the selected resonant vibrational mode.

In yet another aspect, the present invention relates to a system for desorption and ionization of analytes. The system includes a support for holding a sample of analytes in a medium, a laser source emitting light corresponding to a selected vibrational mode of at least one component of the medium, and a plurality of optics elements directing the emitted light to irradiate the sample to cause medium ablation and desorption and ionization of the analytes, an ion accelerator for injecting the ionized analytes into a mass spectrometer, a mass spectrometer which separates the accelerated ionized analytes according to their masses, a detector for the mass determination of ionized analytes separated according to their masses, data collection equipment for recording of the spectrum of determined masses, and data presentation equipment for displaying of the spectrum of determined masses. Additionally, the system includes means for selecting a resonant vibrational mode of at least one component of the medium, and means for tuning an energy source to emit short-pulse radiation substantially at the wavelength of the selected resonant vibrational mode.

These and other aspects will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
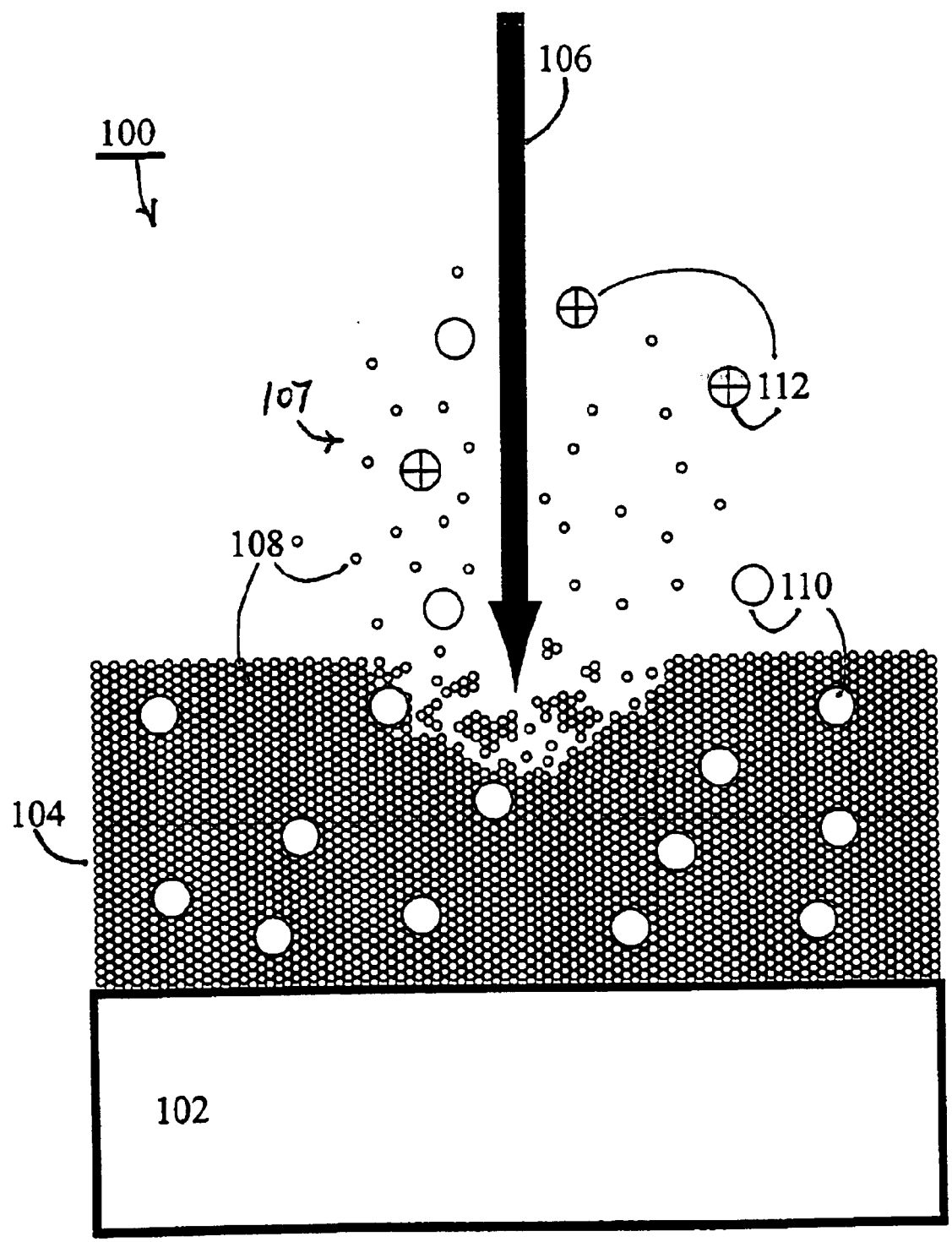
FIG. 1 is a schematic illustration of a configuration of laser desorption and ionization of analytes embedded in an ablation medium according to an embodiment of the present invention.

The present invention is more particularly described in the following embodiments and examples that are intended as illustrative only as numerous modifications and variations therein will be apparent to those skilled in the art. As used in the specification and in the claims, "a" can mean one or more, depending upon the context in which it is used.

Referring generally to FIGS. 1–10, the present invention relates to a system and method for the desorption and ionization of analytes in a medium that utilizes infrared laser desorption and ionization mass spectrometry. In one aspect, the present invention utilizes tunable, ultrashort-pulse laser light in the mid-IR to create spatially dense vibrational excitation in a sample containing analyte proteins, peptides or molecular complexes embedded in a host material medium, by targeting specific vibrational bands of the medium. The molecules to be identified are embedded in a host medium having an infrared absorption spectrum including various vibrational (stretching, bending, librational) modes. A laser tuned to one of those modes is used to deposit sufficient energy in a small volume of the medium to produce bond-breaking, desorption and ablation. As chemical bonds are broken, free charges may be generated during material ablation and plume expansion, sufficient to ionize some of the embedded analyte molecules by charge transfer, impact ionization, or a variety of other thermal, thermomechanical, or photochemical mechanisms. The analyte ions are then focused, extracted and available for identification through any number of standard techniques of ion mass spectrometry, the most common one in practice being time-of-flight (TOF) that is discussed, for example, in "Laser-induced thermal desorption and matrix-assisted methods", *Laser Ionization Mass Analysis*, pp. 127-175, Vertes et al., Wiley Interscience, New York (1993), which is incorporated here by reference for background information only.

This technique may seem to be similar to that used in conventional matrix-assisted laser desorption and ionization (MALDI) mass spectrometry (MS), which is usually carried out with fixed-wavelength nanosecond-pulse-duration lasers emitting light either in the ultraviolet (UV) or infrared (IR) spectral range. However, among other things, the present invention differs sharply from the prior art at least in two important respects. First, rather than adding an exogenous matrix material to the sample to be analyzed, the present invention is practiced by selecting a laser frequency to deposit energy most efficiently into one or more intrinsic vibrational modes of a host medium, which are identified and/or selected prior to the laser radiation. Second, it uses pulses of picosecond or shorter time duration, either singly or emitted as a train of pulses at high pulse repetition frequency. When the laser excitation takes place on time scales short compared to typical medium relaxation times (of order 100 femtosectonds–5 picoseconds), the laser energy can be localized long enough at a single bond in specific vibrational modes to produce bond-breaking, desorption and ionization. This approach avoids many difficulties encountered in conventional IR- and UV-MALDI with nanosecond pulses, because the energy deposition and relaxation mechanisms are simpler and more predictable, while the complications due to laser interactions with the plume do not arise. Moreover, using tunable lasers, one can implement efficient mass spectrometry of proteins not only on all the matrix materials presently available in the UV and IR, but also on many other mediums that do not "work" with the conventional approaches—including electrophoresis gels. Unlike techniques requiring lengthy sample preparation, practicing the present invention is limited intrinsically only in speed by the pulse repetition frequency of the laser.

Thus, among other things, the present invention provides systems and methods for direct sampling of analytes from a medium including electrophoresis gels coupled to mass spectrometry. It is based in part on the discovery that a tunable, ultra short-pulse laser operating in the 2-10 $\mu$m wavelength range can desorb and ionize proteins directly from an electrophoresis gel without addition of exogenous matrix material to the gel or any of a number of other complex sample-preparation steps now in common use. This makes it possible for the first time to incorporate mass spectrometry directly into high-throughput and analysis of biological samples following preliminary separation by any number of electrophoretic and chromatographic techniques.

Little is known about the interactions of ultra short-pulse lasers with materials in the mid-infrared, largely because such laser sources have been unavailable in this range. Recent work has shown that in simple inorganic materials—such as fused silica (glassy $SiO_2$) and simple molecular crystals (e.g., $NaNO_3$ and its isoelectronic cousin $CaCO_3$)—picosecond pulses tuned to a vibrational resonance can bring about explosive vaporization by driving the material to its critical temperature along the non-equilibrium spinodal trajectory. This is discussed in the article "Charged particle emission from dielectric materials initiated by a tunable picosecond mid-infrared laser," Ermer et al., Proc. of SPIE—Intl. Soc. for Opt. Eng. 3935: 104–112 (2000).

There are at least two advantages that are in principle associated with the use of tunable, ultra short laser pulses for desorption and ionization. First, for ultra short pulses in the mid-infrared, the absorption coefficient varies strongly with both laser frequency $\omega$ and intensity I. As discussed in "Mechanisms of laser-induced desorption and ablation," Haglund, Laser Ablation and Desorption pp. 15–138, Academic Press, Boston (1998), any spectroscopic effect, such as ion yield, is proportional to the energy deposited per unit volume:

$$(E/V) \cong F_{laser} \alpha(\omega, I)_{matrix} \quad (1)$$

where F is laser fluence, $\alpha$ is the absorption coefficient, and $\omega$ and I are respectively the laser frequency and intensity. The density of vibrational excitation per molecule—and thus the ability to induce specific reactions, such as ionization—is also controlled by wavelength and intensity.

The second advantage conferred by the use of the ultra short pulses is an enhanced ionization rate. The rate at which a given process occurs, such as ionization, is:

$$\frac{dN^+}{dt} = \eta \cdot N_0 \sigma_{(k)} \cdot I^k \quad (2)$$

where $N^+$ is the number of ions, $\eta$ is a quantum efficiency (which can be taken to include all the loss processes, such as collisions, that reduce the number of ions), $\sigma_{(k)}$ is the kth-order cross section (an effective area) for the ionization process, and I is the laser intensity. For example, a two-photon ionization process would have k=2, and the rate would increase with the square of the laser intensity. Similarly, the higher efficiency for multiphoton processes using ultra short pulse Ti:sapphire lasers is the basis for two-photon fluorescence microscopy. The high intensity enhances the probability for generating a visible photon following excitation by two near-infrared (800 nm) photons, while the low pulse energy and low absorption for single-photon excitation reduces damage to fragile cells and molecules.

Nanosecond lasers typically have higher pulse energies, but lower intensities, than picosecond ("ps") or femtosecond ("fs") pulse lasers; hence the ionization rates associated with ns-laser-induced desorption and ionization should be lower than for ps or fs pulses.

While no aspect of the present invention is bound by a particular theory or mechanism, it is believed that laser pulses tuned to vibrational resonance of the medium are absorbed in such a way as to produce energy localization, bond-breaking, desorption and ionization of the proteins embedded in the medium.

The free-electron laser (FEL) uses the coupling between a relativistic beam of electrons and the spontaneous electromagnetic emissions ("synchrotron radiation") of those electrons traversing a spatially alternating magnetic field to produce coherent light by a purely classical process, rather than the quantum-mechanical excitation of an atomic, ionic or molecular species as one finds in conventional lasers. The temporal pulse structure of the free-electron laser is determined by the characteristics of the electron-beam accelerator. Free-electron lasers are discussed in the articles "Free-electron lasers," Brau, Science 239: 1115–1121 (1988), and "Free-electron lasers: reliability, performance and beam delivery," Edwards et al., IEEE J. Sel. Topics in Quantum Electron. 2: 810–817 (1996).

The FEL used in the experiments performed according to the present invention has a macropulse-micropulse structure reflecting the S-band klystron that powers a free-electron laser located at Vanderbilt University ("the Vanderbilt FEL"). The Vanderbilt FEL delivers laser macropulses at a repetition of rate of 10-30 Hz and is typically operated at 30 Hz. Each macropulse is approximately 5 microseconds ($\mu$s) in duration and comprises micropulses spaced approximately 350 ps apart. The micropulses are approximately 1 ps in duration. Sample irradiation duration is limited by the use of a broad-band electro-optic Pockels cell switch such as that discussed in the article "Broadband Pockels cell and driver for a Mark III-type free-electron laser," Becker et al., Rev. Sci. Intrum. 65: 1496–1501 (1994). Typically, 100 to 800 ns duration portions of the 4 $\mu$s macropulses were allowed for sample irradiation. The Vanderbilt FEL can be tuned to emit light in the wavelength range of 2 to 10 $\mu$m.

In a conventional nanosecond laser, the fluence (areal energy density) and the irradiance or intensity (areal power density) are related simply by the pulse duration of the laser.

In the free-electron laser, on the other hand, the fluence is controlled by the duration of the macropulse, while the peak intensity is set by the micropulse. Previous work has shown that the intensity of the micropulse, rather than the total fluence, determines the course of desorption and ionization as discussed in "Matrix-assisted laser desorption and ionization in the O—H and C=O absorption bands of aliphatic and aromatic matrices: Dependence on laser wavelength and temporal beam profile," Cramer et al., Int. J. Mass Spectrom. Ion Proc. 169/170: 51–67 (1997). This leads to an important conclusion, namely, that the technique developed by the present invention can be applied to all laser systems producing ultrashort infrared pulses.

The solid-state laser technology that made the femtosecond-pulse Ti:sapphire laser into a standard and increasingly affordable turnkey laboratory resource is now moving toward making tunable, ultrashort-pulse mid-infrared lasers at high intensity and high pulse-repetition frequency (~1 kHz) a plausible reality in the next few years. This possibility is the direct result of interest in coherent sources in the mid-infrared for atmospheric sensing of pollutants and other molecular fingerprinting applications, and of rapid progress in the development of new infrared optical materials, including the nonlinear materials needed for parametric amplification processes. Thus, the present invention can be practiced by solid state lasers as well.

Referring now to FIG. 1, a configuration 100 of laser desorption and ionization of analytes, according to an embodiment of the invention, is illustrated. A sample 104 containing both ablation medium and analyte components 110 is arranged on a support 102. A laser-beam 106 from a laser (not shown) irradiates the sample 104 thereby causing to erupt from the sample a 107 plume containing ablated components of the medium 108 and both neutral 110 and ionized 112 analyte molecules. The ionized analyte molecules are then available for electrostatic acceleration into a mass spectrometer (not shown).

Figure 2:
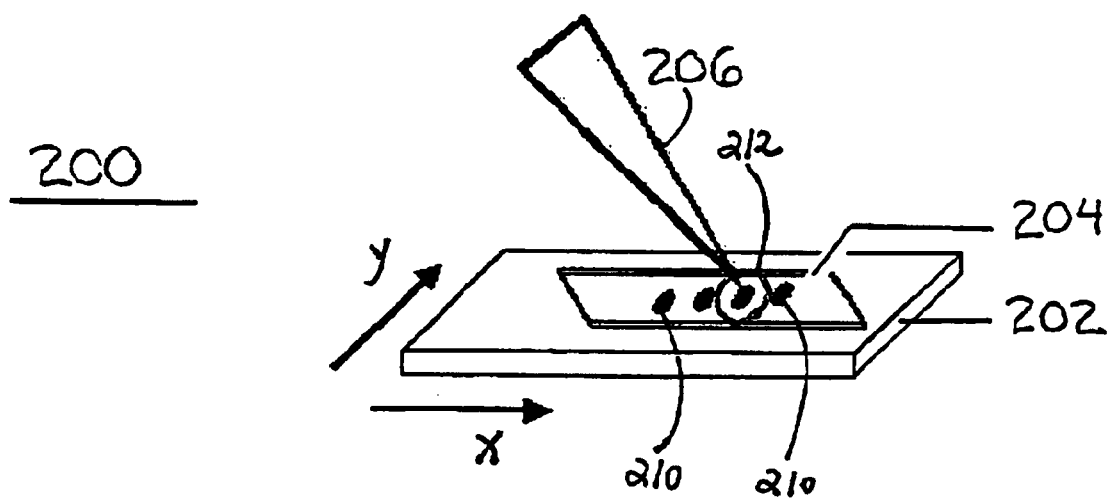
FIG. 2 is a schematic illustration of the irradiation of the locations of spatially separated analytes within an ablation medium according to an embodiment of the present invention.

Referring now to FIG. 2, a configuration 200 of irradiating the locations of spatially separated analytes within a medium, according to an embodiment of the invention, is illustrated. A sample 204 is arranged on a support 202 and is irradiated by a laser-beam 206. The dark spots 210 represent the locations of spatially-separated analytes within the sample 204. The support 202 in this embodiment is capable of movement, independently or jointly, in each of two directions x and y such that the separate analyte locations may be each positioned for irradiation by the laser-beam which is not coplanar with the movement directions. In one embodiment, laser light 206 is focused at a region 212. The support 202 is moved by a driving mechanism (not shown) in a motion back and forth relative to the laser light 206 to form a rastering trace such that each spot 210 of the sample 204 is irradiated by the laser light 206 substantially at the region 212. This allows the desorption and ionization of the analyte to occur substantially at a same region in space for better control and data collection. The sample 204 illustrated contains a section of a polyacrylamide electrophoresis gel. The analytes have been spatially separated by electrophoresis according to molecular weight or charge.

Figure 3:
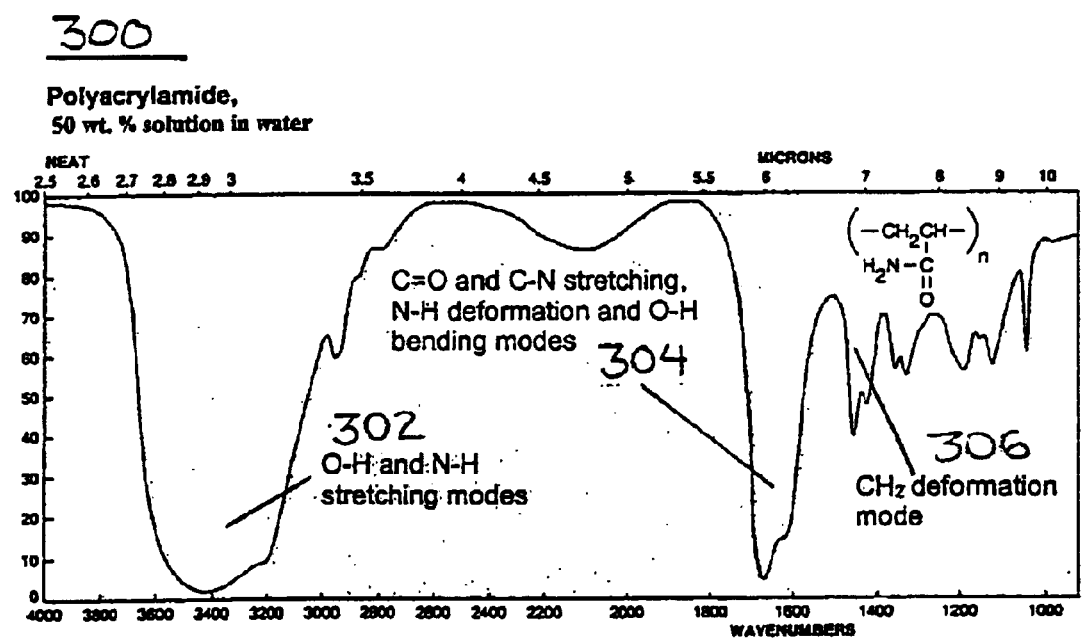
FIG. 3 is the mid-infrared transmission spectrum of polyacrylamide prepared as a 50 weight percent solution in water from prior art.

Referring now to FIG. 3, an exemplary ablation medium transmission spectrum 300 is illustrated. The transmission minima 302, 304, and 306 each correspond to molecular vibrational modes of the components of the medium. Light with a wavelength within the ranges indicated by these minima is maximally absorbed and thus is expected to promote optimal medium ablation. The transmission spectrum in FIG. 3 is that of polyacrylamide prepared as a 50 wt. % solution in water, and is taken from The Aldrich Library of FT-IR Spectra, Edition II, Volume 3, 1997, pg. 4611A. The broad minimum 302 centered around 3 $\mu$m contains the N—H and O—H stretching modes, the latter mode arising both from water and polyacrylamide gel. The minimum 304 centered around 6 $\mu$m reflects the optical properties of the C=O and C—N stretching modes, the N—H deformation modes, and the O—H bending mode. The minimum 306 centered around 6.9 $\mu$m arises primarily from the $CH_2$ deformation mode. Other modes may be contained in these peaks. From the standpoint of laser desorption and ionization, the important characteristics in choosing one of these peaks are (1) the width of the peak, inversely related to the lifetime of the relevant modes; (2) the relative amplitude of the absorption due to each of the modes; and (3) the mechanism(s) of energy partitioning and coupling between modes.

Figure 4:
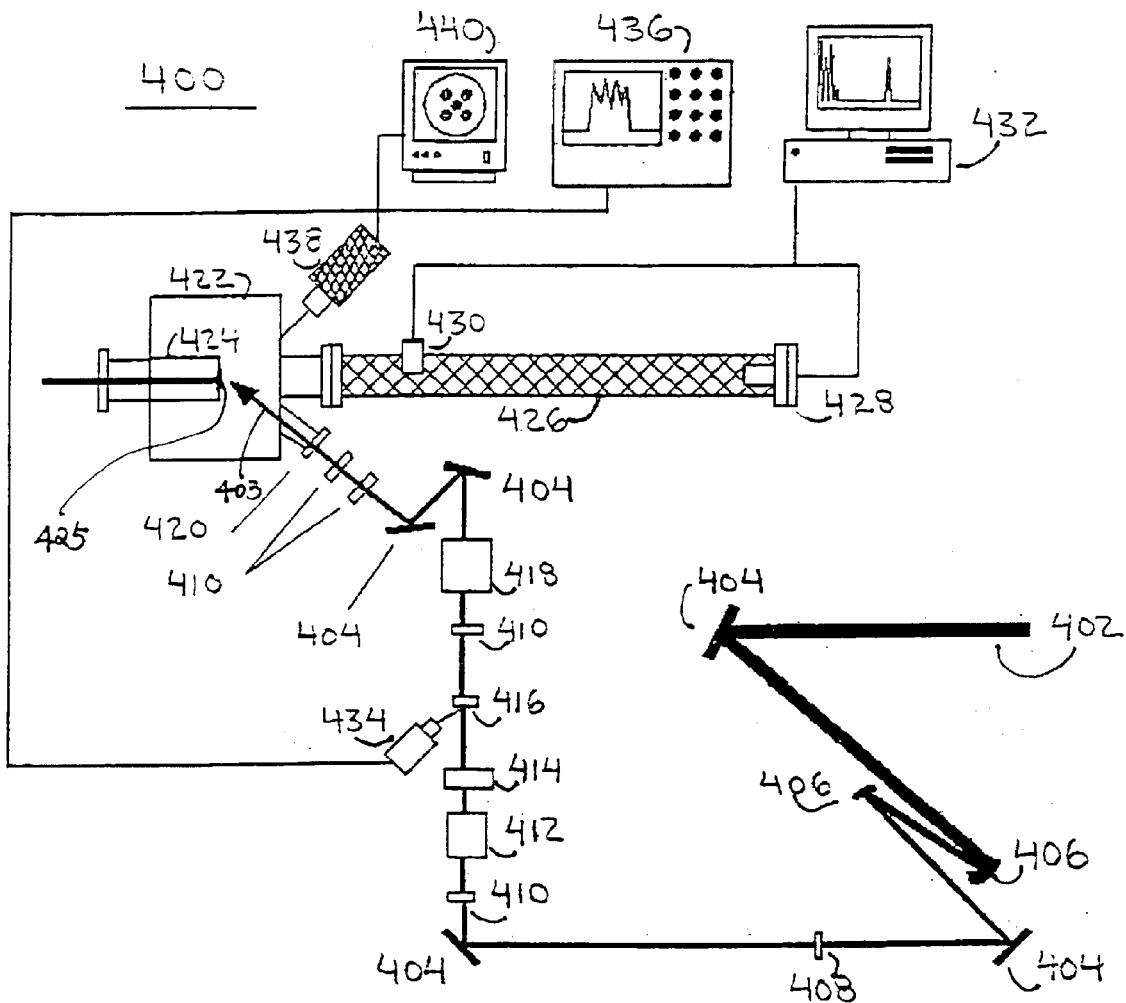
FIG. 4 is a diagram of a laser desorption and ionization sample analysis system according to an embodiment of the present invention.

Referring now to FIG. 4, a system 400 for desorption and ionization of analytes according to one embodiment of the present invention is shown schematically. A beam 402 including FEL and HeNe laser components enters the system 400. Gold-coated planar mirrors 404 and spherical mirrors 406 respectively direct and narrow the beam. Note that several optional mirrors 404 and 406 are utilized in the system 400. Alternatively, more or less mirrors can be utilized to practice the invention. The HeNe laser component is used only for alignment purposes and is removed from the continuing beam by a germanium filter 408 during sample analysis. Optical irises 410 align the FEL beam. A Pockels cell 412, an electo-optic switch, is used to limit the duration of the sample irradiation by the FEL beam to a typical range of 100 to 800 ns. A polarizer 414 is used to attenuate the FEL beam intensity. A mirror periscope 418 raises the beam to the level of the sample support. A lens tube 420 fits into the entrance port of a vacuum chamber 422 and focuses the FEL beam 403 onto the sample 425. The sample 425 is held by the support 424 which may be cooled by liquid nitrogen. Sample irradiation by the FEL beam 403 causes medium ablation and analyte desorption and ionization in the vacuum chamber 422 (see FIG. 1). The analyte ions are accelerated into a flight tube of the mass spectrometer 426. Detectors 428, 430, each having 2 microchannel plates, measure the flight times of the analyte ions. Detectors 28 and 430 are respectively used when the spectrometer 426 is operated in linear and reflectron modes. A computer 432 contains the data acquisition board and signal conversion software to convert the detector signals into mass spectra.

Peripheral systems monitor the irradiation duration and sample region. A BaF beam splitter 416 directs a small portion of the attenuated FEL beam exiting the polarizer 414 onto a photoelectromagnetic (PEM) detector 434. An oscilloscope 436 is used to visualize the PEM detector output in order to monitor the shape and duration of the FEL beam. A camera 438 and a television monitor 440 facilitate the visual monitoring of the sample.

Figure 5:
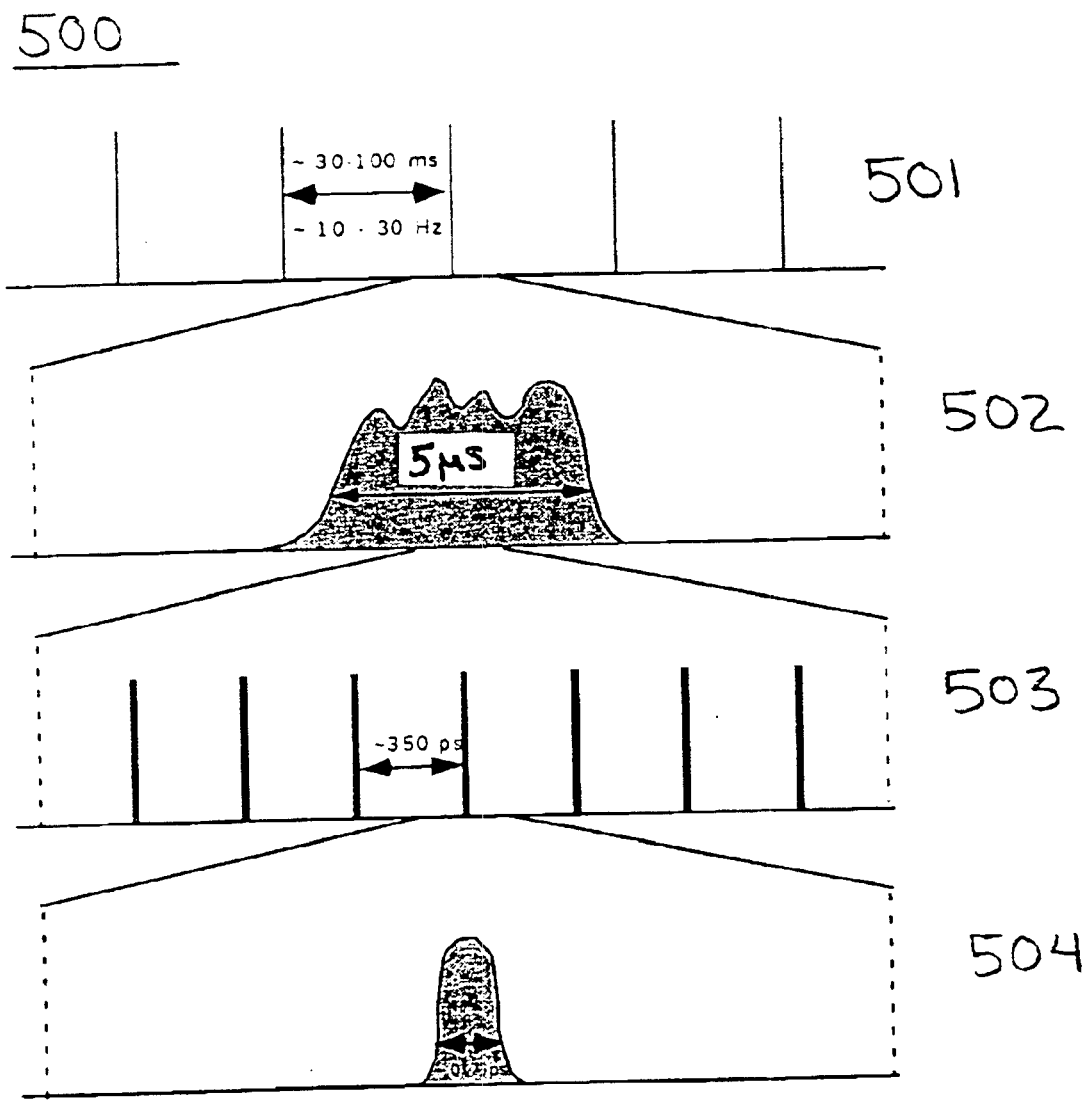
FIG. 5 is a diagram of the pulse structure of a free-electron laser (FEL), which was used as the laser source to acquire the data described in the Examples below according to an embodiment of the present invention.

Referring now to FIG. 5, the Vanderbilt FEL used in the experiments that are discussed below has a macropulse-micropulse structure 500 reflecting the S-band klystron that powers the Vanderbilt free-electron laser. The Vanderbilt FEL delivers a series 501 of laser macropulses 502 at a repetition of rate of 10–30 Hz and is typically operated at 30 Hz. Each macropulse is approximately 5 $\mu$s in duration and has a series 503 of micropulses 504 spaced approximately 350 ps apart. The micropulses are approximately 1 ps in duration. Sample irradiation duration is limited by the use of a broad-band electro-optic Pockels cell switch. Typically, 100 to 800 ns duration portions of the 5 $\mu$s macropulses were allowed for sample irradiation.

Figure 6:
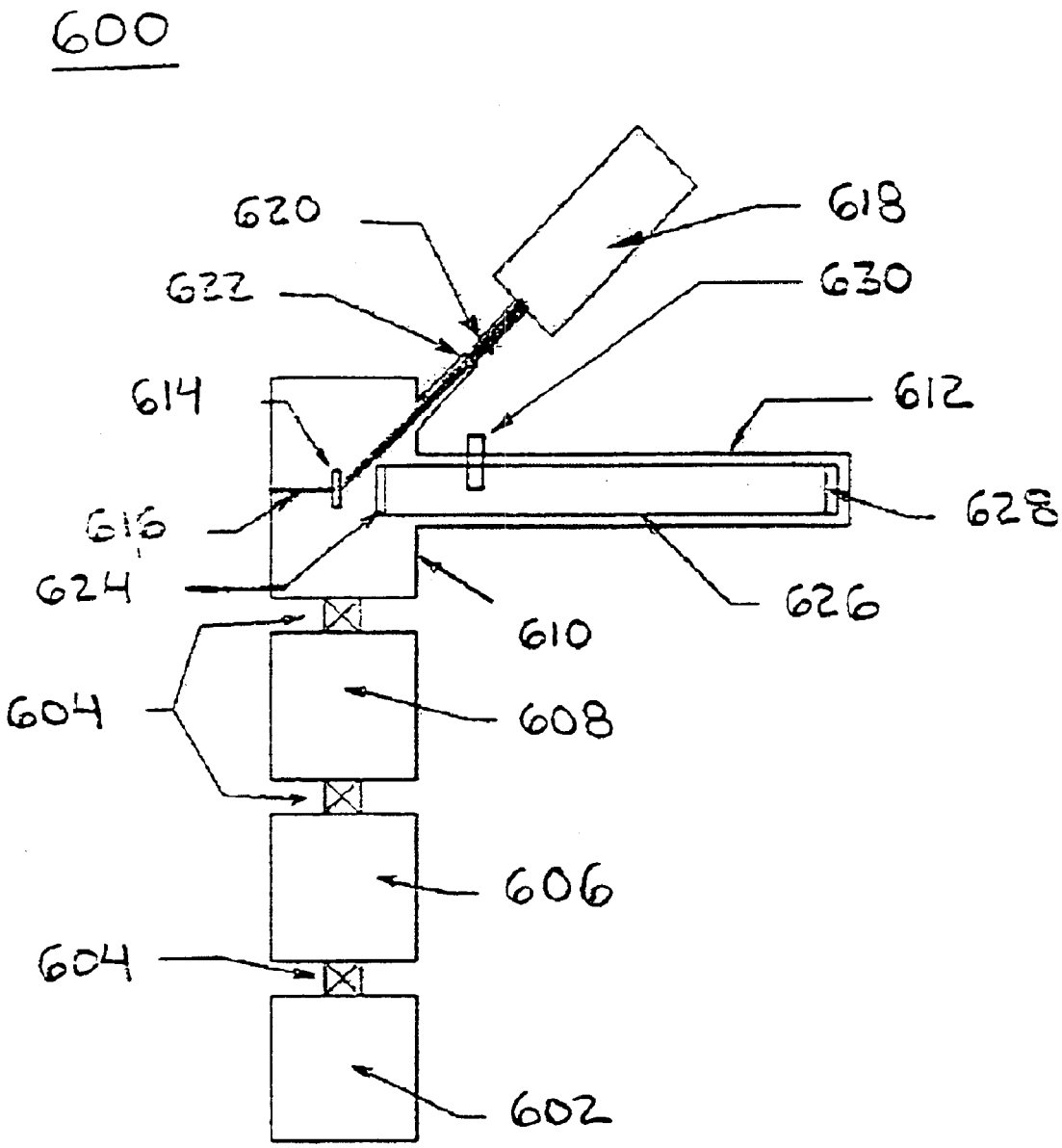
FIG. 6 is a schematic illustration of a laser mass spectrometry apparatus according to an embodiment of the present invention.

Referring now to FIG. 6, a sample processing and analysis system 600 according to one embodiment of the present invention is schematically shown. Samples having analytes and an ablation medium are prepared in an initial processing station 602. For example, biological analytes may be spatially separated in a polyacrylamide gel by electrophoresis. Samples are then stabilized for compatibility with high-vacuum conditions in stabilization station 606. For example, samples may be freezed using the apparatus of FIG. 7 or dried in a low pressure dry nitrogen environment. When used in this specification, the term "freez/freezing/freezed" is interchangeable with the terms "cool/cooling/cooled" or "chill/chilling/chilled" to mean a physical process in which at least part of the sample has an increase in viscosity and a decrease in vapor pressure. Samples are brought to high-vacuum conditions in the sample load-lock station 608 and then passed into the vacuum chamber 610 of the TOF mass spectrometer 612. The various stations are separated by several gate valves 604 that maintain pressure differences when closed. The sample is positioned on a cryo-cooled sample support stage 614 which may be coupled to a 2-axis movable scanning system 616. A laser system 618 is tuned to emit a beam which is focused by optics 620 through a window 622 onto the sample initiating medium ablation and analyte desorption and ionization. The analyte ions are accelerated through ion optics 624 into the TOF tube 626 of the mass spectrometer. The detectors 628 and 630 are utilized in the linear and reflectron spectrometer modes respectively and report to a data acquisition and analysis computer (not shown).

Figure 7:
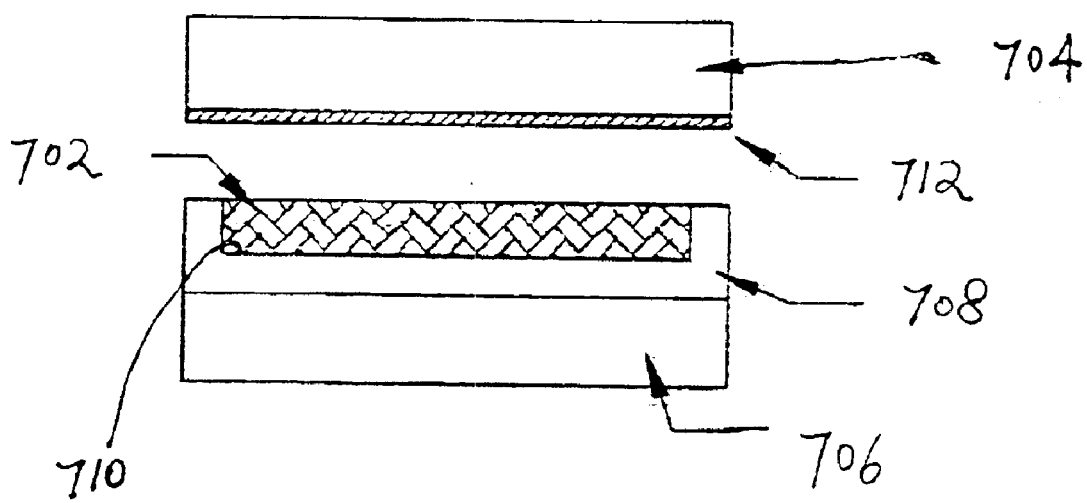
FIG. 7 is a schematic illustration of an apparatus for freezing the sample according to an embodiment of the present invention.

Referring now to FIG. 7, an apparatus 700 for cooling the sample for compatibility with high-vacuum conditions according to one embodiment of the present invention is shown. The apparatus 700 has a first thermal reservoir 704 and a second thermal reservoir 706. A thermally-conducting support 708 is positioned on the second thermal reservoir. The support 708 has a sized recess 710 to receive a sample 702. In use, the sample 702 is positioned in the recess 710 of the thermally-conducting support 708. The sample 702 and support 708 are brought into contact with cryo-cooled thermal reservoirs 704, 706 for cooling. The sample 702 may be separated from directly contacting a thermal reservoir by the placement of an intervening thin release agent 712 which might include, but is not limited to, a thin plastic film, wax paper, or a non-invasive spray lubricant. Each of the thermal reservoirs 704, 706 may contain liquid nitrogen or be in contact with liquid nitrogen. The liquid nitrogen may be substituted by other cooling substances such as liquid helium.

The invention will be better understood by reference to the following illustrative examples, which were conducted according to the present invention.

EXAMPLES

Figure 8:
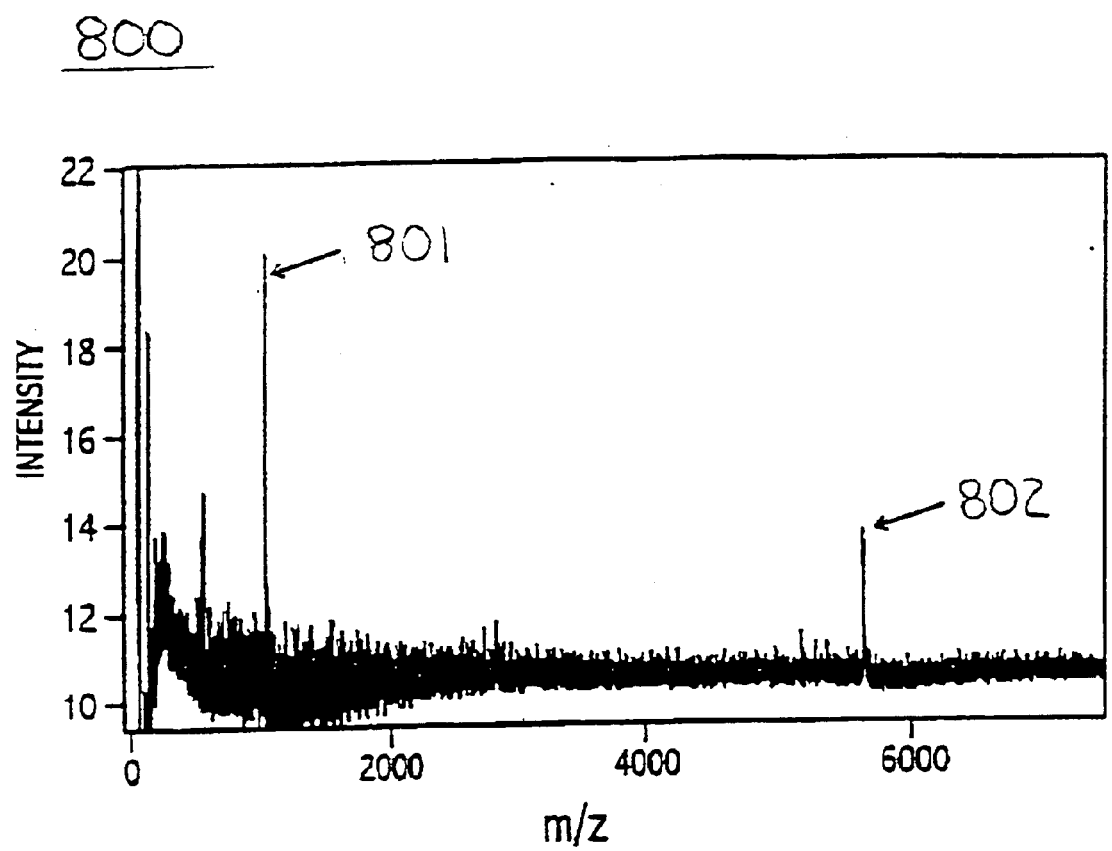
FIG. 8 is a collected mass spectrum acquired from a sample of native polyacrylamide gel with biological analytes according to an embodiment of the present invention using an FEL wavelength of 5.9 $\mu$m.
Figure 9:
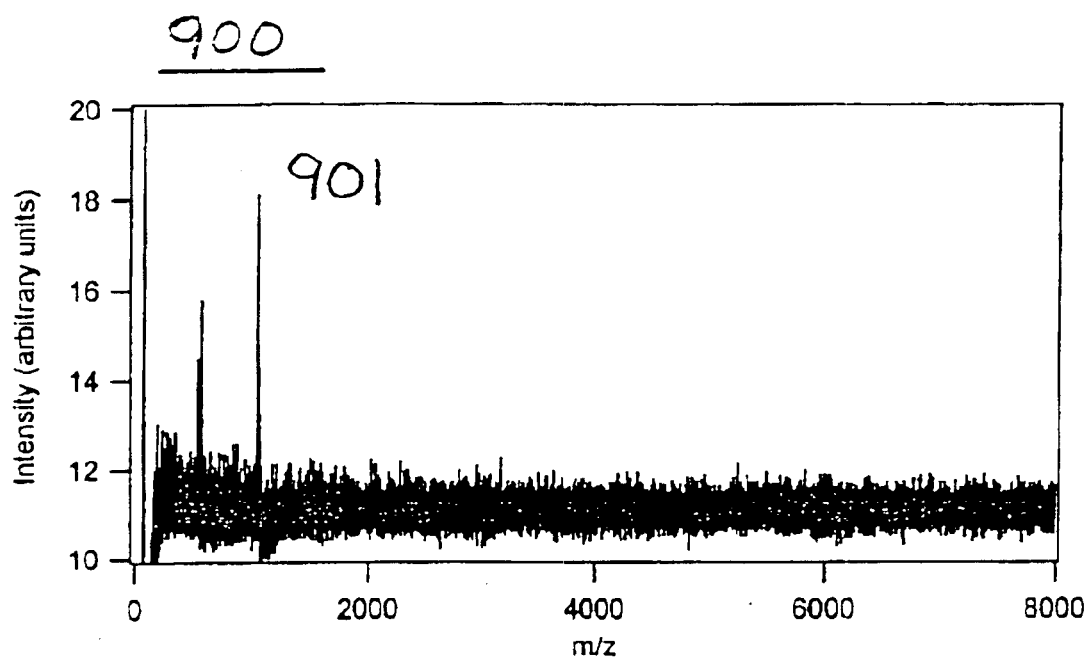
FIG. 9 is a collected mass spectrum acquired from a sample of native polyacrylamide gel with biological analytes according to an embodiment of the present invention using an FEL wavelength of 6.9 $\mu$m.
Figure 10:
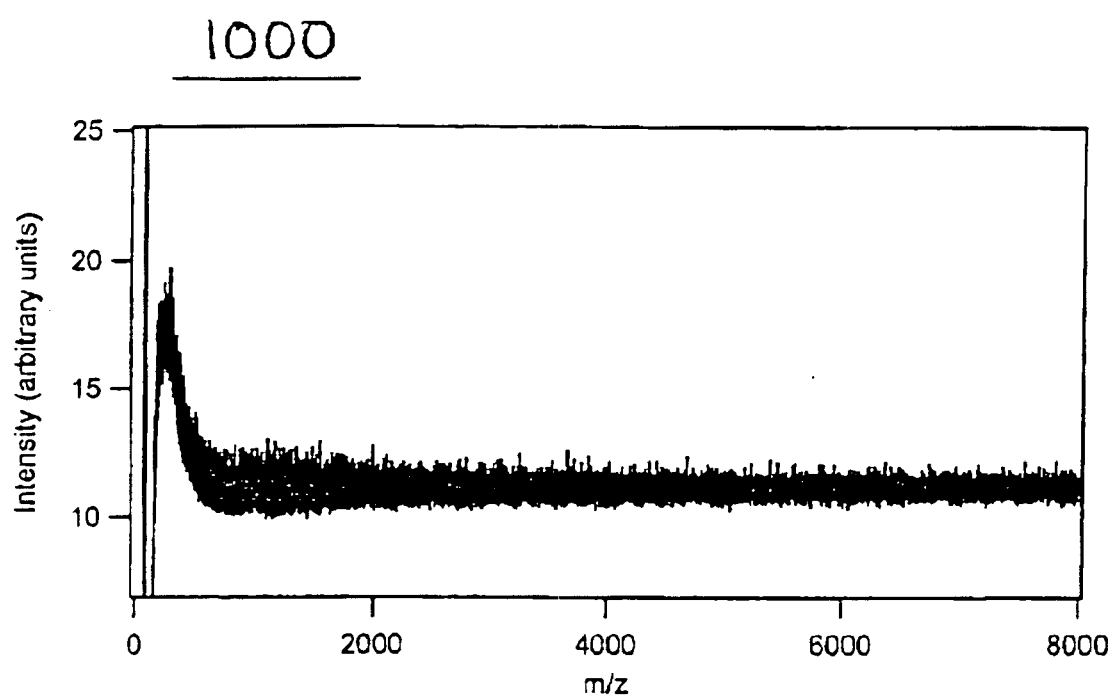
FIG. 10 is a collected mass spectrum acquired from a sample of native polyacrylamide gel with biological analytes according to an embodiment of the present invention using an FEL wavelength of 2.9 $\mu$m.

Experiments were conducted according to the present invention to explore and demonstrate the efficacy of the ultrashort-pulse tunable-laser approach for desorption and ionization of analytes. All of the data given in these examples were acquired using the set-up depicted in FIG. 4. FIGS. 8–10 show several resulting mass spectra and are discussed below.

In each experiment, biological analytes were prepared and applied to a medium in the form of a gel section. Departing from conventional MALDI techniques, the analytes were laser desorbed directly from the gels without any application of exogenous matrix material. After application of the analytes, each gel section was placed in a sample support and immersed into liquid nitrogen for up to 1 minute in order to freeze the gel and make it amenable to insertion into a vacuum chamber. By doing so, the frozen gel section was then directly placed in the vacuum chamber using the cryo-cooled support stage and was irradiated with a pulsed laser beam with a focused diameter of approximately 200 $\mu$m. Note that although gels are used in the experiments, other forms of media that can be utilized to practice the present invention might include, but are not limited to, cellulose acetate, paper, agarose and the like.

The Vanderbilt free-electron laser (FEL) was focused using telescoping mirrors from an original beam diameter of ~1 cm to a diameter of ~3 mm. The beam was then passed through a Pockels cell, an electro-optic switch used to slice out a portion of the 5 $\mu$s FEL macropulse (see FIG. 5). The width of this sliced out portion was variable. The beam was then focused down on the sample in the chamber using a lens.

The ions generated from the sample by the laser pulse were analyzed using a modified TOF mass spectrometer operating in reflectron mode (3 m flight path). This system is equipped with delayed extraction electrode, a dual 25 mm microchannel-plate detector, as well as a cryogenic sample support, which holds samples near liquid nitrogen temperature (77 K). A tunable (2–10 $\mu$m), mid-infrared free-electron laser (FEL) with a 5 $\mu$s macropulse is used, having 1 ps pulses spaced 350 ps apart. A broadband electro-optic Pockels cell switch was used to slice out a 100-800 ns portion of the macropulse. The laser was tuned to wavelengths corresponding to various absorption modes of the polyacrylamide gel medium.

Example 1

The FEL was tuned to a wavelength of 5.9 $\mu$m, corresponding to the C=O and C—N stretching modes, the N—H deformation modes, and the O—H bending mode of the polyacrylamide gel (see FIG. 3). A small gel section, approximately 6 mm in diameter, was cut out of a native 7.5%T Tris-HCl polyacrylamide gel obtained from Bio-Rad Laboratories, Inc., Hercules, Calif. Angiotensin II (MW 1046.2 Da) and bovine insulin (MW 5733.5) analytes were obtained from Sigma Chemical Co., St. Louis, Mo. These analytes were each dissolved in HPLC grade deionized water containing 0.1% trifluoroacetic acid to concentrations of 5 millimolar (mM) and 3 mM, respectively. The deionized water and trifluoroacetic acid were obtained from Fisher Scientific, Fair Lawn, N.J., Equal parts (v:v) of the two analyte solutions were combined. Then approximately 4 microliters ($\mu$L) of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. At this stage, any water in the sample underwent a phase transition to change to ice. The sample was then placed in the vacuum chamber utilizing the cryostage, which had been cooled to liquid nitrogen temperature. The gel section was then irradiated with a 400 ns pulse containing approximately 870 microjoules ($\mu$J) and having a diameter of approximately 200 $\mu$m. FIG. 8 shows a mass spectrum 800 of 100 averaged shots acquired from a native polyacrylamide gel with the FEL at a wavelength of 5.9 $\mu$m. Both Angiotensin II 801 and bovine insulin 802 peaks are clearly visible.

Example 2

The FEL was tuned to a wavelength of 6.9 μm, corresponding to the $CH_2$ deformation mode of the polyacrylamide gel (see FIG. 3). A small gel section, approximately 6 mm in diameter, was cut out of a native 7.5%T Tris-HCl polyacrylamide gel obtained from Bio-Rad Laboratories, Inc., Hercules, Calif. Angiotensin II (MW 1046.2 Da) and bovine insulin (MW 5733.5) were obtained from Sigma Chemical Co., St. Louis, Mo. These analytes were each dissolved in HPLC grade deionized water containing 0.1% trifluoroacetic acid to concentrations of 5 mM and 3 mM, respectively. The deionized water and trifluoroacetic acid were obtained from Fisher Scientific, Fair Lawn, N.J. Equal parts (v:v) of the two analyte solutions were combined. Then approximately 4 μL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with an 800 ns pulse containing approximately 600 μJ and having a diameter of approximately 200 μm. FIG. 9 shows a mass spectrum 900 of 100 averaged shots acquired from a native polyacrylamide gel with the FEL at a wavelength of 6.9 μm, showing desorbed and ionized peaks of angiotens. An Angiotensin II peak 901 is visible. No bovine insulin signal was visible.

Example 3

The FEL was tuned to a wavelength of 2.9 μm, corresponding to the N—H and O—H stretching modes of the polyacrylamide gel (see FIG. 3). A small section, approximately 6 mm in diameter, was cut out of a native 7.5%T Tris-HCl polyacrylamide gel obtained from Bio-Rad Laboratories, Inc., Hercules, Calif. Angiotensin II (MW 1046.2 Da) and bovine insulin (MW 5733.5) were obtained from Sigma Chemical Co., St. Louis, Mo. These analytes were each dissolved in HPLC grade deionized water containing 0.1% trifluoroacetic acid to concentrations of 5 mM and 3 mM, respectively. The deionized water and trifluoroacetic acid were obtained from Fisher Scientific, Fair Lawn, N.J. Equal parts (v:v) of the two analyte solutions were combined. Then approximately 4 μL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 100 ns pulse containing approximately 200 μJ and having a diameter of approximately 200 μm. FIG. 10 shows a mass spectrum 1000 of 100 averaged shots acquired from a native polyacrylamide gel with the FEL at a wavelength of 2.9 μm. Neither an Angiotensin II nor a bovine insulin signal was visible.

Example 4

The FEL was tuned to a wavelength of 5.9 μm, corresponding to the C═O and C—N stretching modes, the N—H deformation modes, and the O—H bending mode of the polyacrylamide gel (see FIG. 3). A small gel section, approximately 6 mm in diameter, was cut out of an SDS-containing 12.5%T Tris-HCl polyacrylamide gel. Angiotensin II (MW 1046.2 Da) and bovine insulin (MW 5733.5) were obtained from Sigma Chemical Co., St. Louis, Mo. These analytes were each dissolved in HPLC grade deionized water containing 0.1% trifluoroacetic acid to concentrations of 5 mM and 3 mM, respectively. The deionized water and trifluoroacetic acid were obtained from Fisher Scientific, Fair Lawn, N.J. Equal parts (v:v) of the two analyte solutions were combined. Then approximately 4 μL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 400 ns pulse containing approximately 400 μJ and having a diameter of approximately 200 μm. A mass spectrum of 100 averaged shots was acquired from the polyacrylamide gel. Angiotensin II and bovine insulin peaks were clearly visible.

Example 5

The FEL was tuned to a wavelength of 6.9 μm, corresponding to the $CH_2$ deformation mode of the polyacrylamide gel (see FIG. 3). A small section, approximately 6 mm in diameter, was cut out of an SDS-containing 12.5%T Tris-HCl polyacrylamide gel. Angiotensin II (MW 1046.2 Da) and bovine insulin (MW 5733.5) were obtained from Sigma Chemical Co, St. Louis, Mo. These analytes were each dissolved in HPLC grade deionized water containing 0.1% trifluoroacetic acid to concentrations of 5 mM and 3 mM, respectively. The deionized water and trifluoroacetic acid were obtained from Fisher Scientific, Fair Lawn, N.J. Equal parts (v:v) of the two analyte solutions were combined. Then approximately 4 μL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with an 700 ns pulse containing approximately 600 μJ and having a diameter of approximately 200 μm. A mass spectrum of 100 averaged shots was acquired from the polyacrylamide gel. An Angiotensin II peak was visible. No bovine insulin signal was visible.

Example 6

The FEL was tuned to a wavelength of 2.9 μm, corresponding to the N—H and O—H stretching modes of the polyacrylamide gel (see FIG. 3). A small section, approximately 6 mm in diameter, was cut out of an SDS-containing 12.5%T Tris-HCl polyacrylamide gel. Angiotensin II (MW 1046.2 Da) and bovine insulin (MW 5733.5) were obtained from Sigma Chemical Co, St. Louis, Mo. These analytes were each dissolved in HPLC grade deionized water containing 0.1% trifluoroacetic acid to concentrations of 5 mM and 3 mM, respectively. The deionized water and trifluoroacetic acid were obtained from Fisher Scientific, Fair Lawn, N.J. Equal parts (v:v) of the two analyte solutions were combined. Then approximately 4 µL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 100 ns pulse containing approximately 190 µJ and having a diameter of approximately 200 µm. A mass spectrum of 100 averaged shots was acquired from the polyacrylamide gel with the FEL. Neither an Angiotensin II nor a bovine insulin signal was visible.

Example 7

The FEL was tuned to a wavelength of 5.9 µm, corresponding to the C=O and C—N stretching modes, the N—H deformation modes and the O—H bending mode of the polyacrylamide gel (see FIG. 3). A small gel section, approximately 6 mm in diameter, was cut out of native 7.5%T Tris-HCl polyacrylamide gel obtained from Bio-Rad Laboratories, Inc., Hercules, Calif. Horse heart cytochrome C (MW 12384) was obtained from Sigma Chemical Co., St. Louis, Mo. The analyte was dissolved in HPLC grade deionized water containing 0.1% trifluoroacetic acid to a concentration 3 mM. The deionized water and trifluoroacetic acid were obtained from Fisher Scientific, Fair Lawn, N.J. Then approximately 4 µL of the analyte solution was applied to the gel section and allowed to remain there for 8 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 400 ns pulse containing approximately 400 µJ and having a diameter of approximately 200 µm. A mass spectrum of approximately 75 averaged shots was acquired from the polyacrylamide gel. Cytochrome C and also doubly charged cytochrome C peaks were visible.

Example 8

The FEL was tuned to a wavelength of 5.9 µm, corresponding to the C=O and C—N stretching modes, the N—H deformation modes and the O—H bending mode of the polyacrylamide gel (see FIG. 3). A small gel section, approximately 6 mm in diameter, was cut out of an SDS-containing 10-20%T Tris-Tricine polyacrylamide gel obtained from Bio-Rad Laboratories, Inc., Hercules, Calif. Melittin (MW 2846.5) and bovine insulin (MW 5733.5) were obtained from Sigma Chemical Co., St. Louis, Mo. The analytes were dissolved in HPLC grade deionized water containing 0.1% triflouroacetic acid to concentrations of 625 µM and 3 mM, respectively. The deionized water and trifluoroacetic acid were obtained from Fisher Scientific, Fair Lawn, N.J. Equal parts (v:v) of the two analyte solutions were combined. Then approximately 3 µL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 400 ns pulse containing approximately 460 µJ and having a diameter of approximately 200 µm. A mass spectrum of 36 averaged shots was acquired from the polyacrylamide gel. Mellitin and bovine insulin peaks were clearly visible.

Example 9

The FEL was tuned to a wavelength of 5.9 µm, corresponding to the C=O and C—N stretching modes, the N—H deformation modes and the O—H bending mode of the polyacrylamide gel (see FIG. 3). A small gel section, approximately 6 mm in diameter, was cut out of an SDS-containing 10-20%T Tris-Tricine polyacrylamide gel obtained from Bio-Rad Laboratories, Inc., Hercules, Calif. Neurotensin (MW 1672.9 Da) and bovine insulin (MW 5733.5) were obtained from Sigma Chemical Co., St. Louis, Mo. The neurotensin was dissolved in 15 mM Tris-HCl to a concentration of 2 mM. The bovine insulin was dissolved in HPLC grade deionized water containing 0.1% trifluoroacetic acid to a concentration of 3 mM. The deionized water, trifluoroacetic acid, and Tris-HCl were obtained from Fisher Scientific, Fair Lawn, N.J. Equal parts (v:v) of the two analyte solutions were combined. Then approximately 4 µL of the combined analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 300 ns pulse containing approximately 330 µJ and having a diameter of approximately 200 µm. A mass spectrum of 35 averaged shots was acquired from the polyacrylamide gel. Neurotensin and bovine insulin peaks were clearly visible.

Example 10

The FEL was tuned to a wavelength of 5.9 µm, corresponding to the C=O and C—N stretching modes, the N—H deformation modes and the O—H bending mode of the polyacrylamide gel (see FIG. 3). A small gel section, approximately 6 mm in diameter, was cut out of an SDS-containing 10-20%T Tris-Tricine polyacrylamide gel obtained from Bio-Rad Laboratories, Inc., Hercules, Calif. Neurotensin (MW 1673.9 Da) was obtained from Sigma Chemical Co., St. Louis, Mo. The neurotensin was dissolved in 15 mM Tris-HCl, obtained from Fisher Scientific, Fair Lawn, N.J., to a concentration of 2 mM. Then approximately 4 μL of the analyte solution was applied to the gel section and allowed to remain there for 10 minutes. The gel section was then rinsed with deionized water and any excess water or analyte solution was removed with an absorbent blotter. No exogenous matrix was added. The gel section was then placed in the sample support and this combination was immersed into liquid nitrogen for up to 1 minute in order to cool the gel and make it amenable to insertion into a vacuum chamber. The sample was then placed in the vacuum chamber utilizing the cryostage, which had been cooled to liquid nitrogen temperature. The gel section was then irradiated with a 100 ns pulse containing approximately 160 μJ and having a diameter of approximately 200 μm. A mass spectrum of 35 averaged shots was acquired from the polyacrylamide gel. A neurotensin peak was clearly visible.

Table I summarizes parts of the results of Examples 1-10 performed according to the present invention.

invention and are not intended to limit the claims to the disclosed elements.

What is claimed is:

1. A method for desorption and ionization of analytes, comprising the steps of:
   a. preparing a sample having analytes and a polyacrylamide medium aving at least one component;
   b. selecting a resonant vibrational mode of at least one component of e medium;
   c. selecting a laser tuned to emit light substantially at the wavelength f the selected vibrational mode; and
   d. irradiating the sample with laser light to cause medium ablation an desorption and ionization of the analytes, wherein the preparing step comprises a step of stabilizing the sample for ompatibility with high-vacuum conditions, wherein the stabilizing step comprises a step of freezing the sample at a sufficiently low temperature so that at least part of the sample has a phase transition.

2. The method of claim 1, wherein the freezing step comprises the steps of placing the sample in a sample support, and immersing the sample support in liquid nitrogen for a period of time so that any water within, the sample changes to ice.

3. A method for desorption and ionization of analytes, comprising the steps of:

TABLE 1

Results of the Examples

| Example No. | Sample analyte(s) | Gel type | No. of shots for average | wave-length (μm) | No. of laser pulses per shot | Pulse peak Intensity (W/cm$^2$) | Pulse peak Fluence (J/cm$^2$) |
|---|---|---|---|---|---|---|---|
| 1 | Angiotensin II and Bovine Insulin | Native (7.5% T Tris-HCl) | 100 | 5.9 | 1143 | $2.4 \times 10^9$ | $2.4 \times 10^{-3}$ |
| 2 | Angiotensin II and Bovine Insulin | Native (7.5% T Tris-HCl) | 100 | 6.9 | 2286 | $8.3 \times 10^8$ | $8.4 \times 10^{-4}$ |
| 3 | Angiotensin II and Bovine insulin | Native (7.5% T Tris-HCl) | 100 | 2.9 | 286 | $2.2 \times 10^9$ | $2.2 \times 10^{-3}$ |
| 4 | Angiotensin II and Bovine insulin | SDS (12.5% T Tris-HCl) | 100 | 5.9 | 1143 | $1.1 \times 10^9$ | $1.1 \times 10^{-3}$ |
| 5 | Angiotensin II and Bovine insulin | SDS (12.5% T Tris-HCl) | 100 | 6.9 | 2000 | $9.5 \times 10^8$ | $9.6 \times 10^{-4}$ |
| 6 | Angiotensin II and Bovine Insulin | SDS (12.5% T Tris-HCl) | 100 | 2.9 | 286 | $2.1 \times 10^9$ | $2.1 \times 10^{-3}$ |
| 7 | Cytochrome C (horse heart) | SDS (12.5% T Tris-HCl) | Approx 75 | 5.9 | 1143 | $1.1 \times 10^9$ | $1.1 \times 10^{-3}$ |
| 8 | Melittin and Bovine insulin | SDS (10–20% T Tris-Tricine gradient) | 36 | 5.9 | 1143 | $1.3 \times 10^9$ | $1.3 \times 10^{-3}$ |
| 9 | Neurotensin and Bovine insulin | SDS (10–20% T Tris-Tricine gradient) | 35 | 5.9 | 857 | $1.3 \times 10^9$ | $1.2 \times 10^{-3}$ |
| 10 | Neurotensin | SDS (10–20% T Tris-Tricine gradient) | 35 | 5.9 | 286 | $1.8 \times 10^9$ | $1.8 \times 10^{-3}$ |

While there has been shown various embodiments of the present invention, it is to be understood that certain changes can be made in the form and arrangement of the elements of the system and steps of the method as would be known to one skilled in the art without departing from the underlying scope of the invention as is particularly set forth in the Claims. Furthermore, the embodiments described above are only intended to illustrate the principles of the present e. preparing a sample having analytes and a polyacrylamide medium having at least one component;
   f. selecting a resonant vibrational mode of at least one component of the medium;
   g. selecting a laser tuned to emit light substantially at the wavelength of the selected vibrational mode; and
   h. irradiating the sample with laser light to cause medium ablation an desorption and ionization of the analytes, wherein the preparing step comprises a step of stabilizing the sample for ompatibility with high-vacuum conditions, wherein the stabilizing step comprises a step of freezing the sample at a sufficiently low temperature so that at least part of the sample has an increase in viscosity and a decrease in vapor pressure.

4. A method for desorption and ionization of analytes, comprising the steps of:
 a. preparing a sample having analytes in a medium including at least one component;
 b. freezing the sample at a sufficiently low temperature so that at least part of the sample has an increase in viscosity and a decrease in vapor pressure ; and
 c. irradiating the frozen sample with short-pulse radiation to cause medium ablation and desorption and ionization of the analytes,
wherein the medium includes an electrophoresis medium.

5. The method of claim 4, further comprising the teps of:
 a. selecting a resonant vibrational mode of at least one component of the medium; and
 b. selecting an energy source to emit short-pulse radiation substantially at the wavelength of the selected resonant vibrational mode.

6. The method of claim 5, wherein the energy source is a laser.

7. The method of claim 6, wherein the laser is a free electron laser.

8. The method of claim 7, wherein the free electron laser is able to generate short-pulse radiation.

9. The method of claim 6, wherein the laser is a solid state laser.

10. The method of claim 9, wherein the solid state laser is tunable to generate short-pulse radiation.

11. The method of claim 6, wherein the laser is a gas laser.

12. The method of claim 6, wherein the laser is a metal vapor laser.

13. The method of claim 5, wherein the step of selecting a resonant vibrational mode comprises a step of locating the resonant vibrational mode from a fourier-transform infrared absorption spectrum of the medium.

14. The method of claim 4, wherein the freezing Step comprises the steps of placing the sample in a sample support, and immersing the sample support in liquid nitrogen for a period of time so that any water within the sample has a phase transition to change to ice.

15. The method of claim 4, wherein the electrophoresis medium comprises polyacrylamide.

16. The method of claim 4, further comprising the steps of:
 a. passing the ionized analytes through a mass spectrometer; and
 b. obtaining a mass spectrum of the ionized analytes.

17. A method for desorption and ionization of analytes, comprising the steps of:
 a. preparing a sample having analytes in a medium including at least one component;
 b. freezing the sample at a sufficiently low temperature so that at least part of the sample has an increase in viscosity and a decrease in vapor pressure ; and
 c. irradiating the frozen sample with short-pulse radiation to cause medium ablation and desorption and ionization of the analytes,
wherein the step of preparing a sample comprises a step of spatially separating the analytes within the medium by electrophoresis.

18. The method of claim 17, wherein the step of irradiating the frozen sample composes a step of irradiating sequentially a plurality of positions within the frozen sample, wherein at least two irradiated positions correspond to locations of the spatially separated analytes.

19. The method of claim 18, wherein each of the plurality of positions is irradiated by radiation delivered in pulses, each pulse having a duration of less than the relaxation time of a selected vibrational mode of at least one component of the medium,
 wherein the pulses are separated in time by intervals, each interval having a duration of at least ten times the relaxation time of the selected vibrational mode.

20. The method of claim 18, wherein each of the plurality of positions is irradiated by radiation delivered in pulses, each pulse having a duration of less than a thermal relaxation time of the at least one component of the medium.

21. The method of claim 18, wherein each of the plurality of positions is irradiated by radiation delivered in pulses, each pulse having a duration of less than a mechanical relaxation time of the at least one component of the medium.

22. A system for desorption and ionization of analytes, comprising:
 a. means for preparing a sample having analytes in a medium including at least one component;
 b. means for freezing the sample at a sufficiently low temperature so that at least part of the sample has an increase in viscosity and a decrease in vapor pressure; and
 c. means for irradiating the frozen sample with short-pulse radiation to cause medium ablation and desorption and ionization of the analytes,
wherein the medium includes an electrophoresis medium.

23. The system of claim 22, further comprising:
 a. means for selecting a resonant vibrational mode of at least one component of the medium; and
 b. means for selecting an energy source tuned to emit short-pulse radiation substantially at the wavelength of the selected resonant vibrational mode.

24. The system of claim 23, wherein the energy source is a laser.

25. The system of claim 24, wherein the laser is a free electron laser.

26. The system of claim 25, wherein the free electron laser is tunable to generate short-pulse radiation.

27. The system of claim 24, wherein the laser is a solid state laser.

28. The system of claim 27, wherein the solid state laser is tunable to generate short-pulse radiation.

29. The system of claim 23, wherein means for selecting a resonant vibrational mode comprises means for locating the resonant vibrational mode from Fourier-transform infrared absorption spectrum of the medium.

30. The system of claim 22, wherein the freezing means includes a sample support to contain the sample, and the sample support being immersed in liquid nitrogen for a period of time so that any water within the sample has a phase transition to change to ice.

31. The system of claim 22, wherein the electrophoresis medium comprises polyacrylamide.

32. The system of claim 22, further comprising means for obtaining a mass spectrum of the ionized analytes.

* * * * *

UNITED STATES PATENT AND TRADEMARK OFFICE
CERTIFICATE OF CORRECTION

PATENT NO. : 6,825,045 B2
DATED : November 30, 2004
INVENTOR(S) : Richard F. Haglund, Jr., David R. Ermer and Michelle Lee Baltz-Knorr It is certified that error appears in the above-identified patent and that said Letters Patent is hereby corrected as shown below:

Column 1,
Lines 11-15, "This invention was made with Government support under a contract awarded by the U.S. Department of Navy and a contract awarded by the U.S. Department of Energy, respectively, and the Government has certain rights in this invention" should read -- This invention was made with Government support under contract N00014-94-1-1023 awarded by the U.S. Department of Navy, contract DE-FG07-98ER62710 awarded by the U.S. Department of Energy and contract F49620-01-1-0429 awarded by the U.S. Department of Air Force, respectively, and the Government has certain rights in this invention. --

Signed and Sealed this

Fifth Day of April, 2005

JON W. DUDAS
*Director of the United States Patent and Trademark Office*